United States Patent
Roberts et al.

(10) Patent No.: US 11,583,281 B2
(45) Date of Patent: Feb. 21, 2023

(54) INTRODUCER FOR UTERINE TAMPONADE ASSEMBLY WITH ECHOGENIC ELEMENT AND METHODS OF USING THE SAME

(71) Applicant: Cook Medical Technologies LLC, Bloomington, IN (US)

(72) Inventors: Erin Roberts, Bloomington, IN (US); Shawn Nichols, Bloomington, IN (US); Wesley Pedersen, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 97 days.

(21) Appl. No.: 16/570,034

(22) Filed: Sep. 13, 2019

(65) Prior Publication Data

US 2020/0093498 A1 Mar. 26, 2020

Related U.S. Application Data

(60) Provisional application No. 62/734,422, filed on Sep. 21, 2018.

(51) Int. Cl.
*A61B 17/12* (2006.01)
*A61B 17/42* (2006.01)
*A61B 17/34* (2006.01)

(52) U.S. Cl.
CPC .. *A61B 17/12099* (2013.01); *A61B 17/12136* (2013.01); *A61B 2017/12004* (2013.01);
(Continued)

(58) Field of Classification Search
CPC ..... A61F 6/146; A61B 1/00082; A61B 17/42; A61B 2017/4216; A61B 2090/3925;
(Continued)

(56) References Cited

U.S. PATENT DOCUMENTS 837,085 A 11/1906 Loar
3,822,702 A 7/1974 Bolduc
(Continued)

FOREIGN PATENT DOCUMENTS

CN 204158457 U 2/2015
DE 4225520 A1 2/1994
(Continued)

OTHER PUBLICATIONS

Office Action and English translation of Korean Application No. 10-2020-7001142 dated Jun. 9, 2021, 11 pages.
(Continued)

*Primary Examiner* — Wade Miles
(74) *Attorney, Agent, or Firm* — Crowell & Moring LLP

(57) ABSTRACT

A device for use with a uterine tamponade balloon catheter apparatus, such as the Bakri postpartum hemorrhage balloon, is disclosed. The device comprises a stylet comprising a hub at its proximal end and an atraumatic tip at its distal end. The device is configured to be removably coupled to the tamponade balloon catheter apparatus to aid in the insertion and positioning of the tamponade balloon catheter within the uterine cavity, allowing the balloon to function as intended for the control and management of postpartum hemorrhage and uterine bleeding. The tamponade balloon catheter includes an echogenic element to aid in visualization by ultrasound during insertion and use. Methods of use of the device are also disclosed.

11 Claims, 4 Drawing Sheets

(52) U.S. Cl.
 CPC .............. *A61B 2017/1205* (2013.01); *A61B 2017/3456* (2013.01); *A61B 2017/4216* (2013.01)

(58) Field of Classification Search
 CPC ........ A61B 17/12136; A61B 17/12099; A61B 2017/4241; A61B 2017/12004; A61B 2017/1205; A61B 2017/3456; A61M 25/0108; A61M 25/0009; A61M 25/0097; A61M 25/0102; A61M 2025/1061; A61M 2025/0063
 See application file for complete search history.

(56) References Cited

U.S. PATENT DOCUMENTS

| | | | |
|---|---|---|---|
| 4,207,891 | A | 6/1980 | Bolduc |
| 4,402,684 | A | 9/1983 | Jessup |
| 4,601,698 | A | 7/1986 | Moulding |
| D286,677 | S | 11/1986 | Osborne |
| 4,753,640 | A | 6/1988 | Nichols et al. |
| 4,826,485 | A | 5/1989 | Johnson |
| 4,964,854 | A | 10/1990 | Luther |
| 5,295,968 | A | 3/1994 | Martel et al. |
| 5,569,222 | A | 10/1996 | Haselhorst et al. |
| 6,135,982 | A * | 10/2000 | Campbell ............. A61M 25/10 604/96.01 |
| 6,245,029 | B1 | 6/2001 | Fujita et al. |
| 6,395,012 | B1 | 5/2002 | Yoon et al. |
| D476,418 | S | 6/2003 | Sprieck |
| 6,740,095 | B2 | 5/2004 | Watson |
| 6,813,520 | B2 | 11/2004 | Truckai |
| D565,192 | S | 3/2008 | Tajima |
| D585,547 | S | 1/2009 | Basleri |
| 7,512,433 | B2 * | 3/2009 | Bernhart ............. A61B 5/0536 600/373 |
| D630,733 | S | 1/2011 | Ahlgren |
| D640,785 | S | 6/2011 | Lee |
| D663,832 | S | 7/2012 | Essinger |
| 8,282,612 | B1 | 10/2012 | Miller |
| 8,287,496 | B2 | 10/2012 | Racz |
| D692,134 | S | 10/2013 | Lee-Sepsick |
| D699,341 | S | 2/2014 | Clark |
| 8,770,200 | B2 | 7/2014 | Ahluwalia |
| D713,957 | S | 9/2014 | Woehr |
| 9,028,401 | B1 | 5/2015 | Bacich et al. |
| 9,067,013 | B2 | 6/2015 | Wright et al. |
| D747,802 | S | 1/2016 | Freigang |
| D748,777 | S | 2/2016 | Uenishi |
| D751,704 | S | 3/2016 | Corydon |
| 9,364,638 | B2 | 6/2016 | Duncan |
| D772,411 | S | 11/2016 | Heath |
| D798,446 | S | 9/2017 | Nino |
| D816,217 | S | 4/2018 | Naughton |
| D846,116 | S | 4/2019 | Naughton |
| D854,148 | S | 7/2019 | Prinz |
| D859,651 | S | 9/2019 | Harding |
| 2002/0133081 | A1 * | 9/2002 | Ackerman ............. A61B 5/4233 600/486 |
| 2004/0030352 | A1 | 2/2004 | McGloughlin et al. |
| 2004/0267203 | A1 * | 12/2004 | Potter ............... A61M 25/0668 604/164.05 |
| 2005/0143689 | A1 | 6/2005 | Ramsey, III |
| 2005/0149060 | A1 * | 7/2005 | Thorstenson ..... A61M 25/0668 606/108 |
| 2005/0256532 | A1 | 11/2005 | Nayak |
| 2006/0015075 | A1 | 1/2006 | Blanco |
| 2006/0173486 | A1 | 8/2006 | Burke et al. |
| 2006/0293612 | A1 * | 12/2006 | Jenson ............... A61B 17/3207 600/585 |
| 2009/0112167 | A1 | 4/2009 | Haarala et al. |
| 2009/0157007 | A1 | 6/2009 | McKinnon |
| 2010/0168511 | A1 * | 7/2010 | Muni ................ A61M 25/0152 600/104 |
| 2011/0060317 | A1 | 3/2011 | Frojd |
| 2011/0118546 | A1 * | 5/2011 | Dillon ............. A61M 25/10186 600/116 |
| 2011/0220120 | A1 | 9/2011 | Frigstad et al. |
| 2011/0259344 | A1 | 10/2011 | Ahluwalia |
| 2013/0204208 | A1 | 8/2013 | Olson et al. |
| 2014/0094773 | A1 | 4/2014 | Lampropoulos |
| 2014/0158138 | A1 | 6/2014 | Ziv et al. |
| 2015/0051634 | A1 | 2/2015 | Kravik et al. |
| 2015/0202411 | A1 | 7/2015 | Duncan |
| 2015/0342641 | A1 | 12/2015 | Belfort et al. |
| 2016/0045719 | A1 | 2/2016 | Ha et al. |
| 2016/0100861 | A1 | 4/2016 | Parys et al. |
| 2016/0106466 | A1 | 4/2016 | Gruber et al. |
| 2016/0151049 | A1 * | 6/2016 | Massengale ........... A61B 8/481 600/458 |
| 2016/0166282 | A1 | 6/2016 | Juravic et al. |
| 2016/0256301 | A1 | 9/2016 | Roeder |
| 2017/0312432 | A1 | 11/2017 | Huang |
| 2018/0256389 | A1 | 9/2018 | Asfar |
| 2018/0360494 | A1 | 12/2018 | Melsheimer |
| 2019/0059947 | A1 | 2/2019 | Bunch et al. |
| 2019/0110797 | A1 | 4/2019 | Melsheimer |

FOREIGN PATENT DOCUMENTS

| | | | |
|---|---|---|---|
| EP | 2905046 | A1 | 8/2015 |
| JP | 2014100303 | A * | 6/2014 |
| JP | 2014100303 | A | 6/2014 |
| WO | WO 00/57943 | A1 | 10/2000 |
| WO | WO 2014/054156 | A | 8/2016 |

OTHER PUBLICATIONS

U.S. Appl. No. 16/003,323, filed Jun. 8, 2018.
U.S. Appl. No. 16/046,327, filed Jul. 26, 2018.
U.S. Appl. No. 16/123,433, filed Sep. 6, 2018.
Design U.S. Appl. No. 29/664,085, filed Sep. 21, 2018.
Examination Report for EP Application No. 18738046.4, dated Dec. 14, 2020, 4 pages.
International Preliminary Report on Patentability and Written Opinion for PCT/US2018/036865, dated Dec. 24, 2019, 8 pages.
Invitation to Pay Additional Fees and Communication Relating to the Results of the Partial International Search for PCT/US2019/051100, dated Dec. 16, 2019, 11 pages.
Office Action and English translation for Japanese application No. 2019-570104, dated Jan. 20, 2021, 12 pages.
International Preliminary Report on Patentability for PCT Application No. PCT/US2019/051100, dated Mar. 23, 2021, 10 pages.
Partial International Search Report for PCT/US2018/036865, dated Aug. 31, 2018, 10 pages.
International Search Report and Written Opinion for PCT/US2018/036865, dated Oct. 23, 2018, 18 pages.
Examination Report for Australian Application No. 2018288595, dated Apr. 20, 2020, 5 pages.
Search Report and the Written Opinion for PCT/US2019/051100, dated Feb. 11, 2020, 18 pages.
Office Action and English translation of Japanese Application No. 2019-570104, dated Jul. 26, 2021, 4 pages.
Examination Report for EP Application No. 18738046 dated Aug. 25, 2021, 4 pages.
Office Action and English translation for Japanese Application No. 2021-539475, dated May 31, 2022, 7 pages.
Office Action and English translation for Chinese Application No. 2022062902841640, dated Jul. 4, 2022, 10 pages.

* cited by examiner

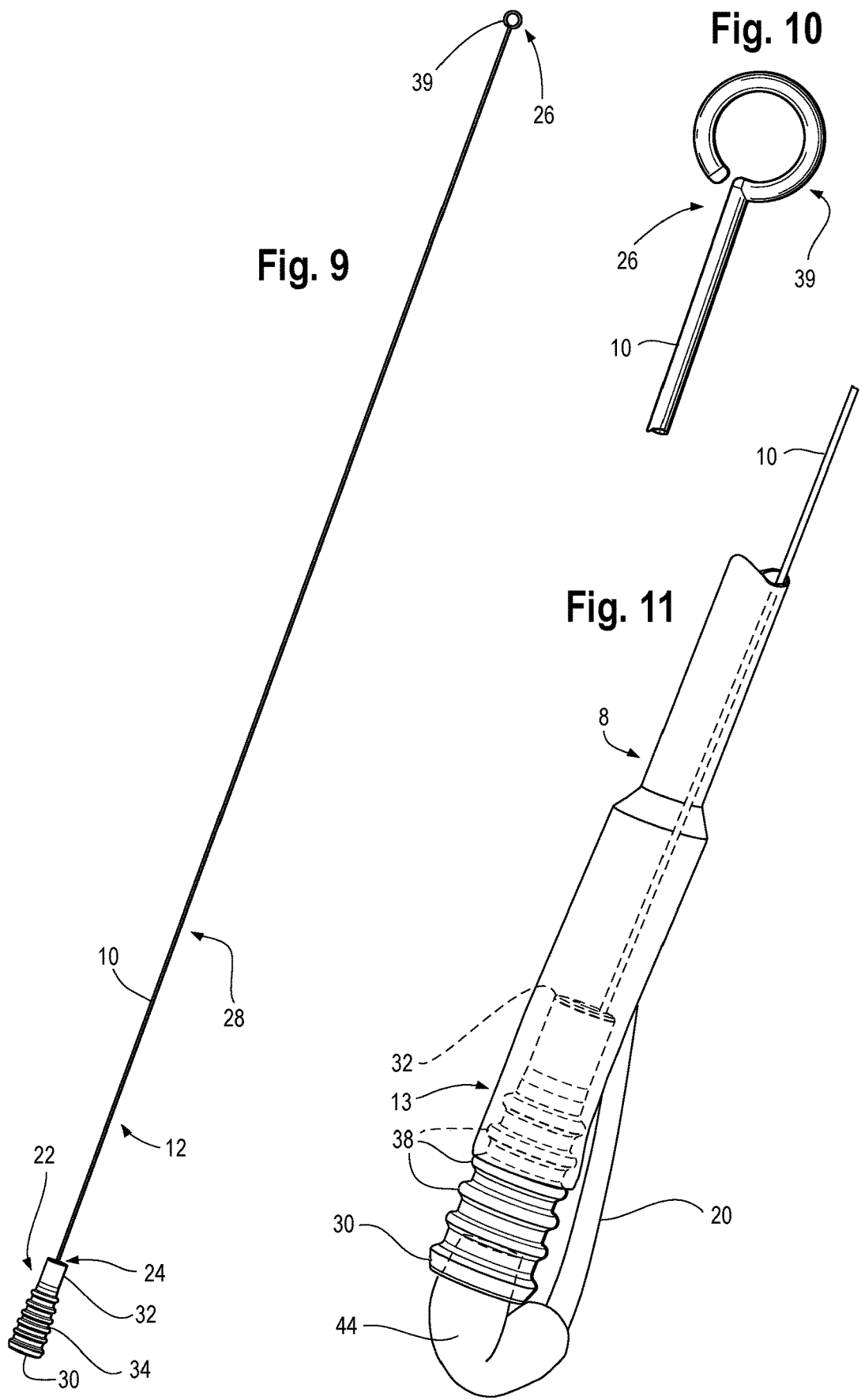

INTRODUCER FOR UTERINE TAMPONADE ASSEMBLY WITH ECHOGENIC ELEMENT AND METHODS OF USING THE SAME

RELATED APPLICATIONS

This application claims the benefit of the filing date under 35 U.S.C. § 119(e) of Provisional U.S. Patent Application Ser. No. 62/734,422, filed Sep. 21, 2018, which is hereby incorporated by reference.

TECHNICAL FIELD

The present invention relates generally to apparatus and methods for controlling uterine bleeding, and more specifically, to an accessory device for use with a uterine tamponade assembly that facilitates proper insertion and positioning of the tamponade assembly within the uterus. The present invention also relates generally to an echogenic component for the uterine tamponade assembly to assist in visualizing and positioning the assembly by ultrasound during use.

Uterine bleeding is a clinical condition attributable to a variety of causes, including postpartum hemorrhages (PPH) following vaginal and/or cesarean childbirth. Postpartum hemorrhage or excessive blood loss after childbirth is commonly caused by uterine atony whereby the uterus fails to contract normally after the delivery of a baby, leading to continuous bleeding. If left untreated, PPH may cause serious complications or even death.

There are a variety of techniques used for treating and managing PPH, including the administration of muscle contracting drugs or agents alone or in combination with other mechanical or surgical techniques. One such technique includes inserting a tamponade apparatus such as a balloon tamponade catheter into the uterus, wherein the balloon is inflated to a sufficient pressure and volume until it conforms generally to the contour of the lower uterine segment. The application of pressure to the interior uterine wall provides a tamponade effect until bleeding is controlled or stopped. One example of a uterine tamponade balloon catheter is the Bakri balloon, Cook Medical Technologies LLC, Bloomington, Ind. The effectiveness of the Bakri balloon may be partially attributable to efficient and proper insertion, placement and inflation, as well as maintaining the balloon in a proper position within the uterine cavity.

In most cases, when use of a balloon tamponade catheter is required, the physician may insert the balloon portion of the catheter into the uterus, making certain that the entire balloon is inserted past the cervical canal and internal ostium. Insertion may be accomplished trans-vaginally following vaginal delivery or trans-abdominally following a cesarean delivery. It is therefore desirable to provide an accessory device, such as an introducer, that can remain in place during use and also serve as a positioner to maintain the proper positioning of the balloon tamponade catheter, which can be used efficiently, effectively, and accurately insert and position the balloon tamponade catheter within a patient's uterus. It is also desirable to provide the balloon tamponade catheter with an echogenic component or element to assist the physician with visualization and placement of the balloon tamponade catheter within the uterus. Accordingly, the disclosed introducer device and/or the disclosed echogenic component can be used with various known uterine tamponade assemblies, such as the Bakri balloon.

The disclosed introducer device may be utilized to rapidly introduce the tamponade assembly into the uterus and remain in place during use of the tamponade assembly. This may allow the balloon to function as intended for the control and management of PPH and uterine bleeding. Advantageously, the disclosed introducer device may therefore provide a desired combination of attributes and characteristics, including, but not limited to, flexibility, torsion and malleability to navigate a patient's anatomy without causing trauma, while also having sufficient pushability and column strength to aid in insertion of the tamponade assembly and allowing adequate drainage if left in place during use of the tamponade balloon assembly. Further, the disclosed echogenic component can provide improved visualization during insertion and assist with accurate positioning and placement of the tamponade assembly in the uterus.

SUMMARY

In one example, the present disclosure describes a positioning device comprising a stylet comprising a longitudinal body having a proximal end and a distal end. A hub is located at the proximal end of the stylet. The hub comprises a proximal end, a distal end and a sidewall extending there between defining a hub lumen, wherein the sidewall comprises a first portion having a first thickness and a second portion comprising a second thickness, wherein the second thickness is greater than the first thickness, and wherein the stylet is coupled to the second portion.

In another example, a catheter assembly is described. The catheter assembly comprises a positioning device comprising a stylet having a proximal end and a distal end and a hub at the proximal end of the stylet. The assembly further comprises a tamponade balloon catheter comprising a catheter having a proximal end and a distal end and at least one lumen extending there between, wherein the catheter comprises at least one echogenic element disposed thereon. The assembly further comprises an expandable tamponade device disposed about at least a portion the catheter. The stylet is configured to extend longitudinally within at least a portion of the at least one catheter lumen.

BRIEF DESCRIPTION OF THE DRAWINGS

FIG. 9 is a perspective view of one example of an introducer device including a hub and a stylet with an atraumatic distal tip attached to the hub.

FIG. 10 is an enlarged view of the atraumatic distal tip of the stylet of FIG. 9.

FIG. 11 is an enlarged view of the proximal end of one example of a tamponade balloon catheter with the side arm thereof inserted into the proximal end of one example of a hub of an introducer device.

DETAILED DESCRIPTION

Throughout this specification, the terms proximal and proximally are used to refer to a position or direction away from, or even external to a patient's body and the terms distal and distally are used to refer to a position or direction towards the patient and/or to be inserted into a patient's body orifice or cavity. The embodiments described below are in connection with an introducer device for use with, or as an accessory to, a tamponade assembly such as a tamponade balloon catheter for treating postpartum hemorrhage, and for introducing and positioning the tamponade balloon catheter in a desired position within the uterus. However, the described introducer device may also be used in connection with a range of medical instruments which are inserted into various body cavities to effectively and efficiently introduce and position such instruments depending on the technique or procedure being performed as will be appreciated by those of skill in the art. The embodiments described below are also in connection with an echogenic element for a tamponade balloon catheter to assist with visualization of the tamponade assembly during the insertion, positioning and placement within the uterus.

Figure 1:
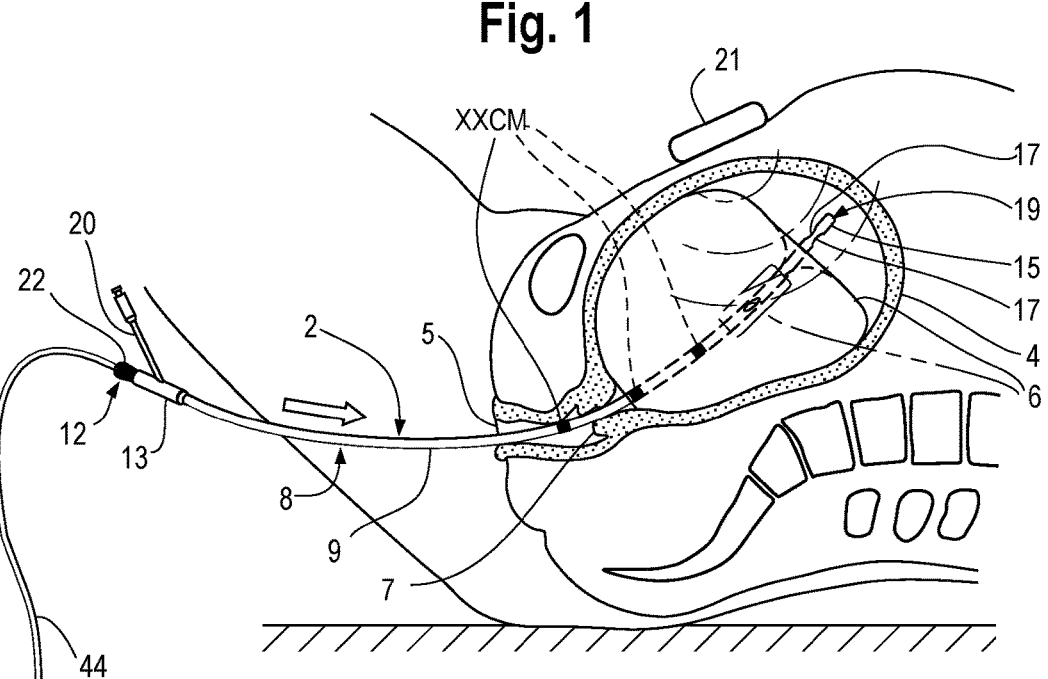
FIG. 1 is a side view of a patient's anatomy showing trans-vaginal insertion and inflation of one example of a tamponade balloon catheter with an example of an introducer device coupled to the tamponade balloon catheter and a drainage assembly coupled to the tamponade balloon catheter.

FIG. 1 illustrates one example of a tamponade assembly, or tamponade balloon catheter assembly 2, inserted and positioned within a patient's anatomy. The balloon is shown in an inflated state in solid lines, and the deflated state is represented by the phantom lines of FIG. 1. A positioning or introducer device 12 extends into the proximal end 13 of the lumen of the tamponade balloon catheter assembly 2. A drainage tube 44 is removably attached to the proximal end of the introducer device 12 leading to a collection bag 11.

Tamponade, which is the closure or blockage of a wound by applying direct pressure to the source of bleeding, is a useful method of stopping or managing bleeding or hemorrhage. One example of a known tamponade assembly includes a Bakri balloon catheter (Cook Medical Technologies LLC, Bloomington, Ind.). The tamponade balloon catheter assembly 2, i.e., a Bakri balloon catheter, is shown as being expanded within the uterine cavity. An introducer device 12 extends within the lumen of the tamponade balloon catheter assembly 2. The introducer device 12 can remain within the lumen of the tamponade balloon catheter assembly 2, therefore also serving as a positioner to maintain the tamponade balloon catheter assembly 2 in place, allowing the user to reposition the tamponade balloon catheter assembly 2 during use.

Figure 8:
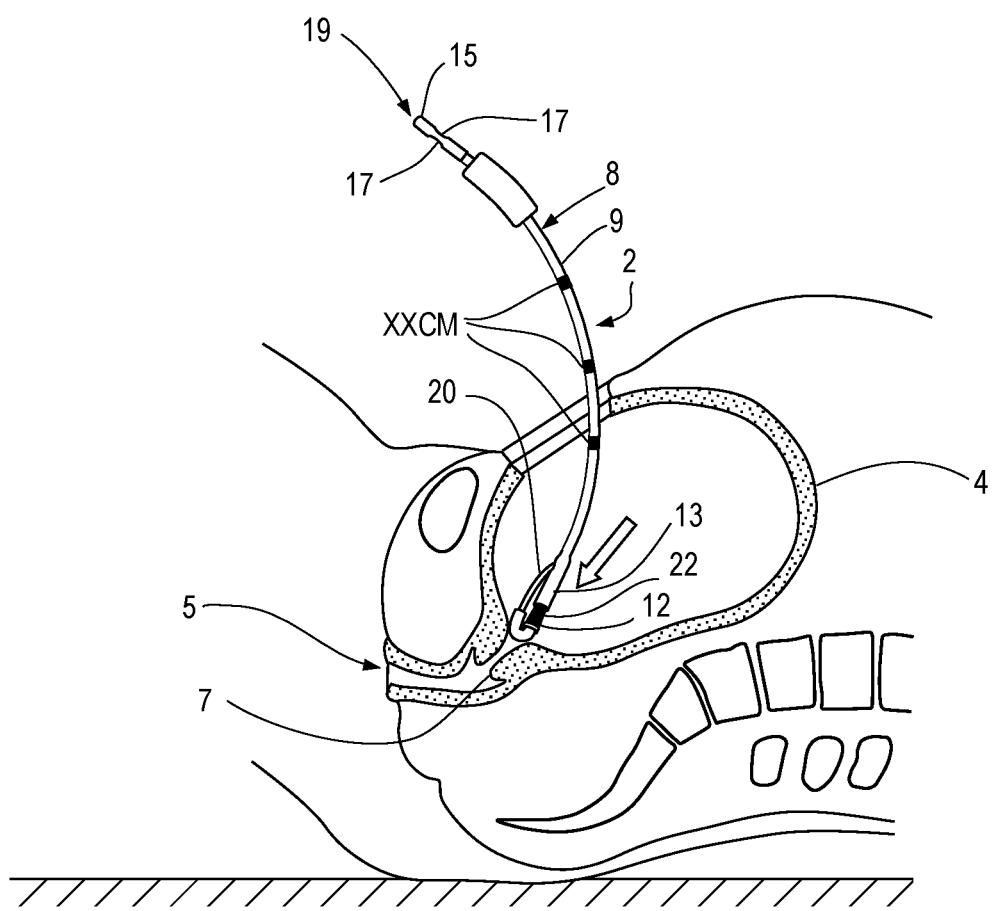
FIG. 8 illustrates trans-abdominal insertion of one example of a tamponade balloon catheter.

As indicated by the arrow in FIG. 1, the introducer device 12 can be used to insert the tamponade balloon catheter assembly 2 vaginally following a vaginal birth. Alternatively, as illustrated in FIG. 8, the introducer device 12 can be employed to introduce the tamponade balloon catheter assembly 2 trans-abdominally following a cesarean birth. As shown by the arrow in FIG. 8, the introducer device 12, coupled with the tamponade balloon catheter assembly 2, can be introduced through the cesarean opening in the patient's abdominal wall and into the uterus 4. The proximal end 13 of the tamponade balloon catheter assembly 2 can then be pulled through the vaginal canal until the base of the balloon 6 (which is in a deflated state in FIG. 8) contacts the internal cervical ostium. Before inflation of the tamponade balloon catheter assembly 2, the incision may be closed, being careful not to puncture the uninflated balloon 6 while suturing.

While the tamponade balloon catheter assembly 2 is intended for placement in the uterine cavity 4 of a patient for treating and controlling postpartum hemorrhage (PPH), it may also be used in various other locations, lumens or orifices within the body, including vessels, bones, organs or other tissues, as necessary or desired. Its dimensions are alterable so that it may be appropriately dimensioned to navigate to the uterus 4, or any other target body cavity, from which fluid, such as blood, will be drained. As shown in FIG. 1, the tamponade balloon catheter assembly 2 preferably includes a catheter 8 having a longitudinal body 9 and a distal end 15 and a proximal end 13.

There is a drainage lumen 16 extending along the length of the longitudinal body 9 between the proximal 13 and distal 15 ends and, in one example, a connector (such as a Y-connector or any other suitable connector) may be located at the proximal end 13 of the catheter 8 for connecting the catheter 8 to a source of air or saline for inflation of the balloon 6 and/or for connecting the catheter 8 to a collection bag 11 or receptacle for receiving waste, fluid and/or blood drained from the patient. The catheter 8 may include one or more openings 17 at or near its distal end 15, such that when the distal end 15 of the catheter 8 is positioned in the uterus 4, the openings 17 allow blood and other fluids to enter and flow through the drainage lumen 16. The drainage lumen 16 may also be used to introduce irrigation fluid or other material into the uterus 4, such as to flush the openings 17 at the distal end 15 of the catheter 8 should they become blocked with clotted blood, tissue or other debris. The catheter 8 may also include additional ports or orifices at various points along the longitudinal body 9 to allow blood or other fluid to enter the catheter 8. The catheter 8 may also be provided with one or more depth markers on and/or along the length of the shaft to further aid in positioning and placement. For example, as shown in FIG. 1, a plurality of lines, rings or other similar types of markings are located at several spaced apart locations along the catheter, identified with measurements such as "XX cm" for example. Such markings provide a visual indication to the physician regarding the distance of measure, length and/or depth of insertion and position of the catheter 8 within the uterus.

Figure 2:
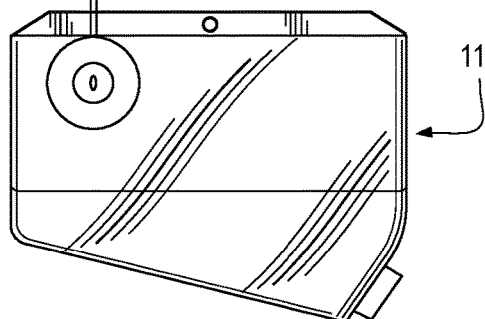
FIG. 2 is an enlarged view of the distal end of the tamponade balloon catheter of FIG. 1 having one example of an echogenic element.
Figure 2:
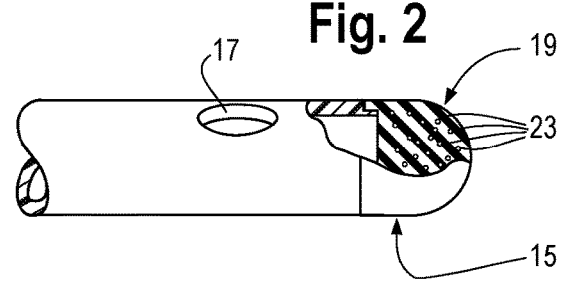

As shown in FIG. 2, the catheter 8 may include one or more components that assist and/or enhance visualization of at least part of the tamponade balloon catheter assembly 2. In one example, this may include providing the tamponade balloon catheter assembly 2 with an echogenic structure or element 19. An echogenic element 19 may include any structure that enhances visualization of one or more portions of the tamponade balloon catheter assembly 2. The echogenic element may then be viewed via ultrasound, such as by an ultrasound device, transducer or wand 21 as shown in FIG. 1. More specifically, echogenicity is the ability to bounce an echo, or return a signal in ultrasound examinations. Echogenicity is higher when the surface bouncing the sound echo reflects the sound waves. Tissues or elements that have higher echogenicity are usually represented with lighter colors on images in medical ultrasonography. In contrast, tissues or elements with lower echogenicity are usually represented with darker colors. Thus, a visible difference in contrast will be displayed where there is an interface of elements or tissues with different echogenicities. As such, providing one or more echogenic elements provide the advantage of providing the physician the ability to have a real-time enhanced view of the location and position of the tamponade balloon catheter assembly during introduction and placement as well as during use and withdrawal. This may also improve patient comfort, success rates, safety, efficiency and results of a particular procedure.

The echogenic element 19 may be integrally formed with the tamponade balloon catheter assembly 2. Alternatively, the echogenic element 19 may be separately formed or manufactured and then attached to the tamponade balloon catheter assembly 2. Such attachment may be accomplished by adhesives, bonding, over-molding, RF welding, mechanical attachment or other suitable attachment mechanisms. The tamponade balloon catheter assembly 2 may be provided with a single echogenic element 19 or a plurality of echogenic elements 19 as necessary or desired.

Figure 3:
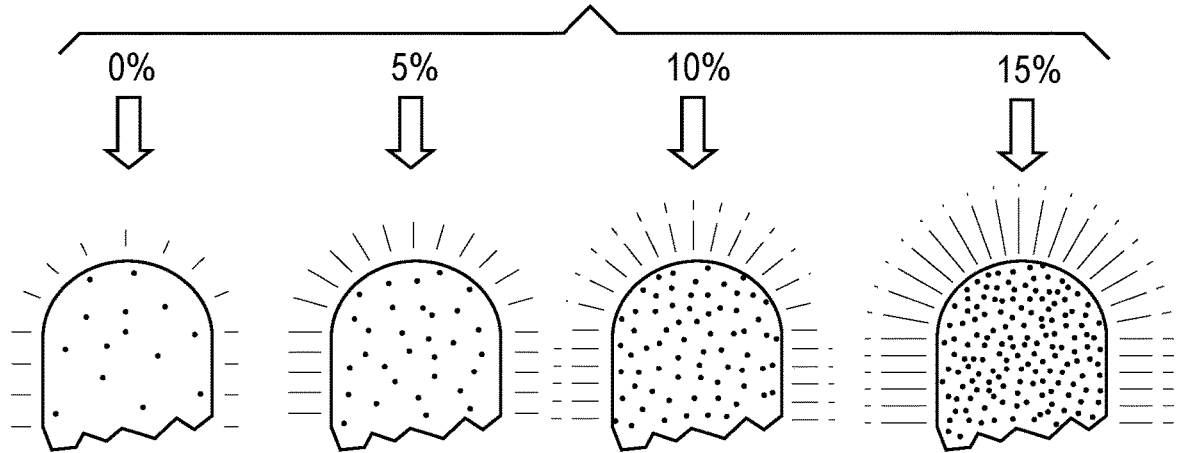
FIG. 3 illustrates the visualization of the distal tip of a plurality of tamponade balloon catheter assemblies by ultrasound, with each tip having varying amounts of echogenicity.

In one example, the tamponade balloon catheter assembly 2 may include an echogenic element 19 located at the distal end 15 of the catheter 8. As shown in FIGS. 2 and 3, a plurality of echogenic beads 23 are present on the distal end 15 of catheter 8. In one example, the echogenic beads 23 may be formed of glass and may be embedded in a polymeric material that is over-molded on to the distal end 15 of the shaft of catheter 8. The polymeric material into which the polymeric beads 23 may be embedded, attached to or otherwise adhered may include rubbers, plastics and/or other compliant materials that may be over-molded, shaped or formed over the distal end 15 of the catheter 8. In one non-limiting example, the polymeric material may include silicone. The echogenic beads 23 may include a molecular coating. Such a molecular coating may allow the beads 23 to better adhere or bond to the polymeric material, including silicone, to which they are embedded or adhered to. One example of glass echogenic beads 23 are supplied by Potters Industries LLC.

It is contemplated that the echogenic beads 23 may be a variety of shapes, sizes and dimensions. It is also contemplated that the beads 23 may be formed by other materials that have echogenic properties. In other examples, an echogenic element 19, such as a sphere, disk or dome which may form a single solid echogenic tip on the distal end 15 of catheter 8 may be used. One or more additional echogenic elements 19 may also be present at one or more locations along the length of the catheter 8 and/or on the balloon catheter assembly 2. For example, cylindrical bands or other markings that have echogenic properties may be present on, or applied to, the surface of the catheter 8 and/or the balloon catheter assembly 2.

The echogenic element 19 may be present in varying quantities, percentages, densities or amounts at one or more locations on the tamponade balloon catheter assembly 2. In one example, a greater percentage by volume (a higher concentration) of echogenic beads 23 may be present at the distal end 15 of the catheter 8, which may intensify ultrasound reflection. A greater percentage by volume of the echogenic element 19 may result in a greater or increased visualization of the particular portion of the tamponade balloon catheter assembly 2 on which the echogenic element 19 is present when viewed under ultrasound. As shown in FIG. 3, for example, four distal ends 15 (distal tips) of four different balloon catheter assemblies are shown as viewed by ultrasound. Each distal end 15 has a different percentage by volume of an echogenic element 19 present.

More specifically, the four separate distal ends 15 each have a different percentage or concentration of echogenic beads 23 that have been embedded in a polymeric material and then over-molded on to the distal end 15 of a tamponade balloon catheter assembly 2. It is the tip of the distal end 15 of each tamponade balloon catheter assembly 2 that is shown in FIG. 3. The first (left-most) distal tip has no echogenic element 19 present. In other words, the distal end 15 has no echogenic beads 23 or other echogenic element 19 present. The image shown second from left has a 5% by volume concentration of echogenic beads 23 embedded in a polymeric material which is over-molded on to the distal end 15 of the catheter 8. The image shown third from left has a 10% by volume concentration of echogenic beads 23 embedded in a polymeric material which is over-molded on to the distal end 15 of the catheter 8. Finally, the image shown on the far right has a 15% by volume concentration of echogenic beads 23 embedded in a polymeric material which is over-molded on to the distal end 15 of the catheter 8. In one example, the percentage concentration of echogenic beads 23 may be about 5% to about 10% by volume concentration of echogenic beads 23 embedded in silicone which is over-molded on to the distal tip or end 15 of the catheter 8.

It will be appreciated that a greater or lesser concentration of one or more echogenic elements 19 may be used as necessary or desired. It will also be appreciated that different echogenic elements 19 in varying concentrations may be located at different positions on or along the tamponade balloon catheter assembly 2. This may depend, for example, upon what portion(s) of the tamponade balloon catheter assembly 2 the user may wish to increase or enhance visualization by ultrasound during insertion and placement of the assembly 2. In one non-limiting example, an echogenic element 19 may be positioned at one or more locations along the length of the catheter 8. This may be a single echogenic element 19 or more than one. A single echogenic element 19 along the longitudinal body 9 of the catheter 8 may be larger in size or diameter, while a plurality of echogenic elements 19 may be present at the distal end 15 of the tamponade balloon catheter assembly 2 as described above in the form of a plurality of echogenic beads 23.

A tamponade structure, such as a balloon 6, is located near the distal end 15 of the catheter 8, and is preferably made of an expandable material such as rubber, silicone, latex or any other expansible biocompatible material. Other tamponade mechanisms may also be used in lieu of or in addition to the balloon 6, such as plurality of arms, tubes, loops, mesh or similar structures capable of expanding or otherwise conforming to the uterine cavity 4. As shown generally in FIGS. 6 and 7, an inflation lumen 14 within the catheter 8 is provided to allow for inflation and deflation of the balloon 6. The inflation lumen 14 may run parallel with the drainage lumen 16, but preferably, the two lumens 14, 16 remain separate for their entire lengths and the respective lumens may generally be the same size and have similar inner diameters or, alternatively, the respective inflation lumen 14 and drainage lumen 16 may have different sizes, dimensions and/or inner diameters.

Figure 6:
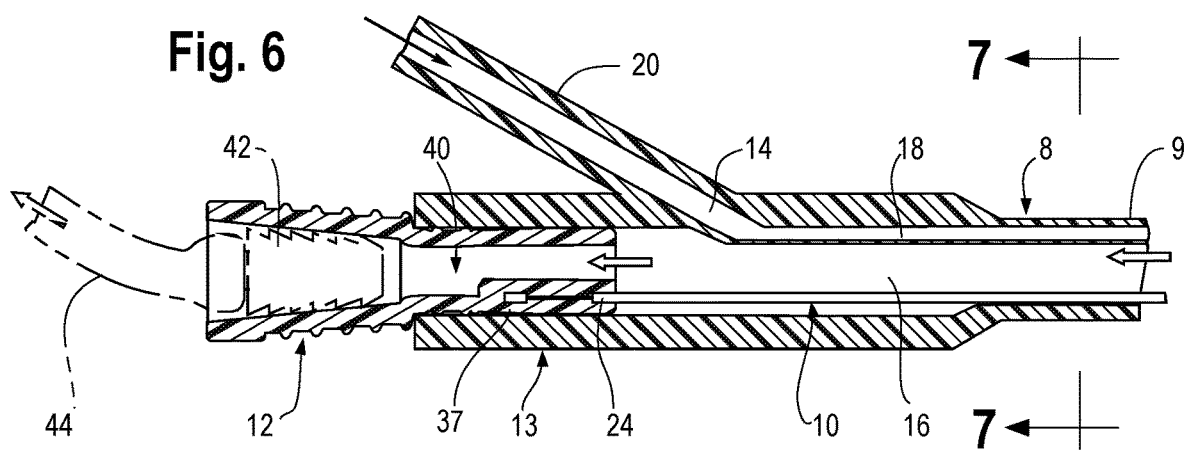
FIG. 6 is a side cross-sectional view of one example of the proximal end of a tamponade balloon catheter with a hub and stylet removably coupled thereto, and a drainage tube removably coupled to the proximal end of the hub.
Figure 7:
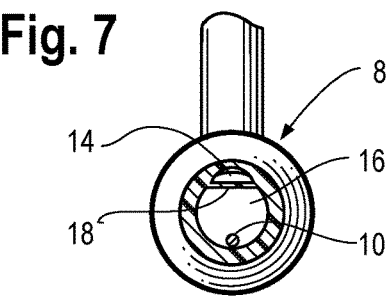
FIG. 7 is a cross-sectional view of one example of a tamponade balloon catheter shown in FIG. 6.

In one example, as shown in FIGS. 6 and 7, the drainage lumen 16 may be larger than the inflation lumen 14, such that the inner diameter of the drainage lumen 16 is shown as being greater than the inner diameter of the inflation lumen 14. In one embodiment, the inner diameter of the drainage lumen may be about 0.215 inches, although other dimensions greater or smaller are contemplated. Further, in one example, a septum or separating wall 18 separates the inflation lumen 14 and the drainage lumen 16. The placement of the septum 18 results in each of the inflation lumen 14 and the drainage lumen 16 generally having a "D" shaped cross-section. However, the shape and relative size of the respective lumens 14, 16 can vary, as can the placement of the septum 18 that separates the lumens 14, 16, such that the respective lumens can have approximately the same inner diameter or different inner diameters as necessary or desired.

As shown in at least FIGS. 1, 6 and 8, the proximal end 13 of the catheter 8 may include a branch or side arm 20. Alternatively, if a "Y" connector mentioned above is used, this can be one branch of the "Y" connection. As shown in cross-section in FIG. 6, this side arm 20 is in fluid communication with the inflation lumen 14. Various media, such as water, saline, air or other physiologically compatible medium, may be introduced through the inflation lumen 14 to facilitate controlled expansion of the balloon 6. When connected to an inflation source, such as a saline bag, saline filled syringe or other inflation source, the inflation media can be introduced into the inflation lumen 14 through the side arm 20 allowing it to flow in a distal direction through the lumen of the catheter 8 and into the balloon 6, thus facilitating balloon expansion.

Once the balloon 6 has been placed within the uterus 4 of the patient, the balloon 6 may be inflated or otherwise expanded. Preferably, the balloon 6 has sufficient compliance such that, when expanded, it conforms generally to the shape and contour of the cavity in which it is placed, and when deflated, can be sufficiently reduced in profile to provide for easy passage and removal through the cervix 7 and vagina 5 (or, in the case of a cesarean birth, through the abdominal incision as shown in FIG. 8). The size and volume to which the balloon 6 may expand is preferably determined by the body cavity where hemorrhage control is needed. As shown in FIG. 1, the balloon 6 is preferably inflated with a sufficient volume and pressure such that it conforms generally to the contours of the uterine cavity 4, and more specifically, to the lower uterine segment. The inflated balloon 6 then exerts a generally uniform compressive force or pressure upon the uterine wall to substantially reduce or even stop the uterine bleeding or hemorrhage. It may also be possible to coat or impregnate all or at least a portion of the balloon surface that comes into contact with the uterine wall with biocompatible materials, drugs or other substances that may enhance or assist in controlling uterine bleeding. In one non-limiting example, this may include muscle contracting or clotting enhancing drugs or other substances that facilitate inflation/deflation of the balloon 6.

As mentioned above, the tamponade balloon catheter assembly 2 may include one or more other components or accessories. In one example, this may include an introducer device 12. The introducer device 12 may be integrally formed with and/or coupled to the tamponade balloon catheter assembly 2. Thus, an assemblage of the tamponade balloon catheter assembly 2 and the introducer device 12 can be provided to a physician directly out of the package. Alternatively, the introducer device 12 may be a separately provided component that can be inserted into catheter 8 of the tamponade balloon catheter assembly 2 and removably coupled to the proximal end 13 of the tamponade balloon catheter assembly 2 prior to or during use of the tamponade balloon catheter assembly 2.

The introducer device 12 may comprise a stylet 10 with a hub 22 located at the proximal end of the stylet 10, as shown generally in FIGS. 1, 6 and 8. The stylet 10 may provide structure or added rigidity to the catheter 8 and, as previously mentioned, may be integrally formed within the catheter or, alternatively, the stylet 10 may be inserted into the catheter 8 by a physician prior to or during use of the tamponade balloon catheter assembly 2. Preferably, the stylet 10 extends longitudinally within the drainage lumen 16 as shown in FIGS. 6 and 7, or alternatively through the inflation lumen 14 or through an additional or separate lumen of the catheter 8. In one non-limiting example, the stylet 10 may be a solid rod or mandrel as shown in FIGS. 9 and 10. However, the stylet 10 may be of other shapes or dimensions as necessary or desired, such as a hollow tube or cannula with a lumen extending there through, which provides an additional drainage conduit through which blood or other fluids draining from a body cavity, such as uterus 4, can flow.

Figure 4:
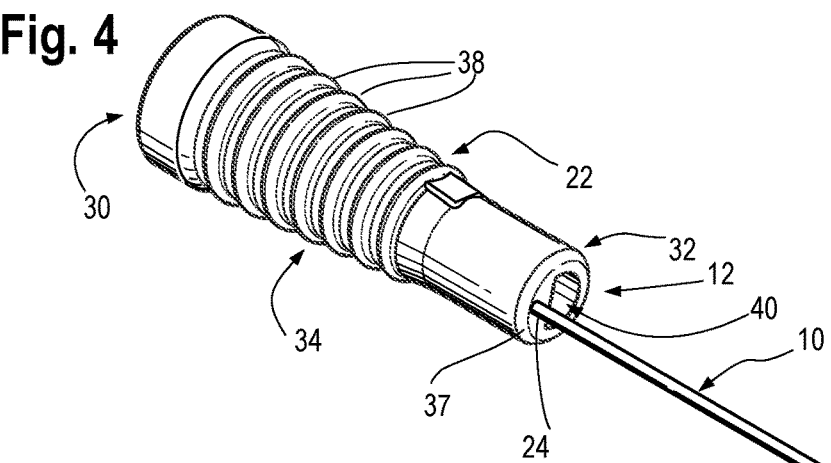
FIG. 4 is a perspective view of one example of an introducer device, including a hub and a stylet extending from the hub.
Figure 5:
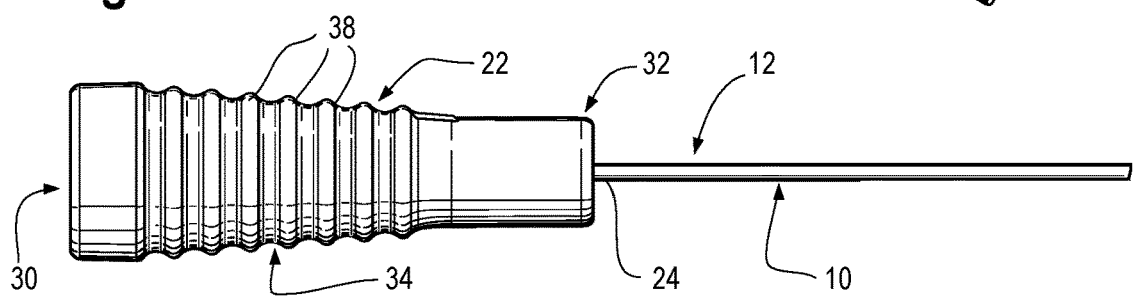
FIG. 5 is a side view of one example of an introducer device comprising a hub and stylet extending from the hub.

As shown in FIGS. 4, 5 and 9 in one embodiment, the stylet 10 may comprise a rod-like structure comprising metals, plastics and/or other materials that provide sufficient rigidity to maintain column strength and bolster the catheter 8, yet still flexible enough to navigate a patient's anatomy. In one example, the stylet 10 may be a stainless steel rod. It is also contemplated that the stylet 10 may be formed of other metals or metal alloys including, for example, shape memory alloys including nitinol. The stylet 10 has a proximal end 24, a distal end 26 and a middle section 28 located between the proximal and distal ends 24, 26. The length of the stylet may be in the range of about 47 cm to about 53 cm and preferably about 50 cm, but other suitable lengths are contemplated as necessary and desired. The outer diameter of the stylet may be about 0.015 inches to about 0.125 inches and, in one example, preferably about 0.04 inches. It is advantageous to provide a stylet 10 having a minimal outer diameter such that fluid and/or tissue flowing through the drainage lumen 16 can also flow efficiently and freely around the outer surface of the stylet 10, when the stylet 10 remains in place within the drainage lumen 16 of the catheter 8, as shown in FIG. 7. In one example, the outer diameter of the stylet will be less than half (50%) of the inner diameter of the drainage lumen 16. In another example, the outer diameter of the stylet will be less than one quarter (25%) of the inner diameter of the drainage lumen 16. In yet another example, the outer diameter of the stylet will be less than 10% of the inner diameter of the drainage lumen 16. In a further example, the outer diameter of the stylet will be less than 5% of the inner diameter of the drainage lumen 16.

The stylet 10 can therefore be left in place within the drainage lumen 16 of catheter 8 during use of the tamponade balloon catheter assembly 2 to treat hemorrhage. In other words, the introducer device 12 does not have to be removed from the lumen of the tamponade balloon catheter assembly 2 in order to allow fluid to drain from the uterine cavity 4. However, if necessary or desired, the introducer device 12 can be removed from the tamponade balloon catheter assembly 2 during use and then re-inserted into the lumen of the catheter 8 to aid in the repositioning and/or removal of the tamponade balloon catheter assembly 2 when hemorrhage ceases and use of the tamponade balloon catheter assembly 2 is complete. Other shapes, dimensions and configurations of the stylet 10 are contemplated as necessary to provide the desired combination of attributes and characteristics, including, but not limited to, column strength, stiffness, torsion, flexibility and malleability of the stylet 10 for the intended use.

The stylet 10 may run the entire length or at least a portion of the length of the catheter 8, and extend to a location adjacent to or just distal of the openings 17 at the distal end 15 of the catheter 8, for example, or at least extend a sufficient length so as to add longitudinal stability to the catheter 8. Sufficient column strength of the stylet 10 provides pushability while reducing or substantially eliminating unwanted folding and/or bending of the catheter 8, while also resisting and preventing longitudinal shortening, shrinkage and/or collapse during trans-vaginal insertion (and/or insertion through a C-section incision) and during positioning of the balloon 6 within the uterus 4. The stylet 10 also has sufficient flexibility and malleability so as to navigate the contours of a patient's anatomy without causing damage, perforation, tearing or trauma.

As shown generally in at least FIGS. 4-6, the introducer device 12 may further comprise a hub portion 22 at the proximal end 24 of the stylet 10. The hub 22 comprises a proximal end 30 and a distal end 32 and a sidewall 34 extending there between that defines a lumen 40. In one example, the outer diameter of the hub 22 may be about 0.313 inches at its distal end 32 at or near where the hub 22 is coupled to the stylet 10. The distal end 32 of the hub 22 may be integrally formed with the proximal end 24 of the stylet 10 or it may be separately formed and attached to or over-molded on to the stylet 10 such as by bonding, adhesives and/or other suitable attachment mechanisms. In one example, a molten hub may be over-molded over the proximal end 24 of the stylet 10. In one example, the proximal end 24 of the stylet 10 may be flattened and/or widened to provide a greater surface area to which the hub 22 may be over-molded or otherwise attached to the stylet 10 as shown in FIG. 6. The hub 22 may be coaxial with the axis of the stylet 10 or the hub 22 may be offset or angled from the proximal end 24 of the stylet 10. As shown in FIG. 4, the stylet 10 may extend from one side or wall of the distal end of the hub. The sidewall 34 of the hub may have a generally uniform thickness or it may have a varied thickness, with one or more portions being thicker than other portions. For example, the portion of the hub sidewall 34 where the stylet 10 is not attached may be thinner than where the stylet 10 attaches to the sidewall 34. The thinner portion of the sidewall 34 may be about 0.068 inches, while the thicker portion 37 of the sidewall 34 where the stylet 10 attaches to the hub 22 may be about 0.120 inches. In one non-limiting example, the thicker portion 37 of the hub sidewall 34 may include about 0.040 inches on one side of the stylet 10, plus the thickness of the stylet 10 itself being 0.040 inches in diameter, and then another thickness of about 0.040 inches on the other side of the stylet 10 for a total thickness of approximately 0.120 inches. Thus, when viewing the hub 22 in a perspective view as shown in FIG. 4, the distal end 32 of the hub 22 may have an outer diameter of about 0.313 inches which includes the thinner portion of the sidewall 34 of 0.068 inches, plus the diameter of the D-shaped hub lumen 40 (which may be approximately 0.125 inches) plus the 0.120 inch thickness of the thickened portion 37 of the hub sidewall 34 where the stylet 10 attaches to the hub 22. These dimensions are exemplary and not intended to be limiting, as other dimensions are contemplated as one of skill would appreciate. The thickened portion 37 of the hub sidewall 34 may provide a sufficient attachment area for the stylet 10 to be attached to the hub 22.

The distal end 26 of the stylet 10 may comprise an atraumatic tip 39. The atraumatic tip 39 reduces or eliminates the risk of scraping, puncturing, tearing or damaging the inner surface of the catheter 8 with the distal end 26 of the stylet 10 when the introducer device 12 is inserted into the drainage lumen 16. In one example, the distal end 26 of the stylet 10 may be over-molded with a softer material, such as rubbers, plastics or other elastomeric materials, so that the distal end 26 of the stylet 10 is compliant, soft, bendable and therefore atraumatic. In another example, the distal end 26 of the stylet 10 may comprise a sphere, disc, ball or bead or other similar rounded structure formed of metals, plastics, rubbers or combinations of one or more materials. The ball may be solid or it may include dimples or one or more holes may be formed therein, similar to a "whiffle ball" configuration. In yet another example shown in FIGS. 9 and 10, the distal end 26 of the stylet 10 may be bent or rounded to form a loop, ring, lasso or eyelet type structure. The eyelet shaped distal tip 39 shown in FIGS. 9 and 10 may be formed from the same material used to form the stylet 10 or it may be formed of different materials or combinations thereof.

In one example, the hub 22 may be formed of a biocompatible elastomer, including but not limited to a polymeric molding or casting having a durometer soft enough to be pliable and provide for sealing with other components or fittings (such as a drainage tube 44 and/or drainage fitting 42) yet stiff enough to have pushability during insertion of the introducer device 12 into the patient during use. The hub 22 may be formed of a polymer such as urethane or silicone or it may be formed of a co-polymer. Other materials may also be used to form the hub 22 including elastomers such as silicone and rubbers and/or plastics. In one example, the hub 22 may be formed of a nylon blend (such as Pebax®, for example). The hub 22 may have a durometer of approximately 25 D to approximately 40 D. It is contemplated that the thicker wall 37 of the hub 22 to which the stylet 10 is attached may be formed of a different material or an additional material(s), be reinforced or have a different durometer than other portions of the hub 22. This could provide a stronger, sturdier or more stable portion of the hub 22 to accommodate stylet attachment. The thicker wall 37 may extend the entire length or distance between the proximal and distal ends 30, 32 of the hub 22 or the thicker wall 37 may extend only partially between the proximal and distal ends of the hub 22. As shown in one example in FIG. 6, the thicker wall ends from the distal end 32 of the hub 22 towards the proximal end 30, where it is coupled to the proximal end 24 of the stylet 10. Further, the thickened portion 37 of the hub sidewall 34 may extend partially around the circumference of the hub 22. In another example, the thickened portion 37 extends around the entire circumference of at least a portion of the hub 22.

As illustrated in FIGS. 4-6, the proximal end 30 of the hub 22 may be flared radially outwardly, such that the proximal end 30 has a greater outer diameter than the distal end 32 of the hub 22 which may taper radially inwardly. One or more ribs, threads or ridges 38 may be present on at least a portion of the exterior surface of the hub 22. In one non-limiting example as shown in FIG. 5, a plurality of ridges 38 extend around the sidewall of the hub 22 in ring-like protrusions, and the proximal end 30 of the hub 22 comprises a generally smooth surface, free of such ridges 38. The ridges 38 may enhance the gripping surface for the user when manipulating the introducer device 12 and/or inserting or removing the hub 22 of the introducer device 12 into and from the proximal end 13 of the catheter 8, while the generally smooth proximal end 30 also provides enhanced stability and structure as well as a gripping surface. It should be appreciated that the number of ridges as well as their shape, (dis)continuity, and relative angle to each other and the longitudinal axis of the hub 22 are provided as one example, where other configurations will provide a desirable enhanced gripping functionality while remaining within the scope of the present embodiments, yet providing a very different visual appearance. For example, the surface could include one or more features instead of or in addition to the ridges shown and described, such as knurled surfaces; rectangular, hexagonal, or otherwise-cornered geometric-sectioned circumferential or non-circumferential ribs/ridges that can be straight, zig-zag, or differently oriented; convexly and/or concavely dimpled surfaces; and other surface configurations known to provide for improved gripping function.

As shown in FIG. 6, the tapered distal end 32 of the hub 22 is preferably shaped for removable attachment or coupling to the proximal end 13 of the catheter 8. For example, the ribbed exterior surface at or near the distal end 32 of the hub 22 may be inserted into (or otherwise engaged with, such as by barbs, threads and/or other corresponding engageable surfaces) the proximal end 13 of the catheter 8 as shown in FIG. 6. In this way, the tamponade balloon catheter assembly 2 and the introducer device 12 can be coupled and move together as a unit to provide convenient and efficient insertion, positioning and repositioning of the tamponade balloon catheter assembly 2 in the uterus 4. The distal end 32 of the hub 22 may remain in place within the proximal end 13 of the catheter 8 such as by interference fit or friction fit or corresponding threads, barbs or sealing surfaces located within the proximal end 13 of catheter 8, although other methods of attachment between the respective components may also be used.

The hub 22 may have at least one lumen 40 formed therein. The hub lumen 40 may be formed in any portion of the hub 22 between the proximal and distal hub ends 30, 32, however, as shown in FIG. 4 and FIG. 6, the hub lumen 40 extends between the proximal and distal ends of the hub 22 to allow fluid to flow freely through the hub 22. The hub lumen 40 also provides an aperture into which a drainage fitting 42 can be removably attached to the proximal end 30 of the hub 22, as shown in FIG. 6. In one example, the drainage fitting 42 is a barb fitting but it is contemplated that any fitting for removable attachment with the hub lumen 40 may be used.

Alternatively or in addition to providing a lumen 40 for placement of a drainage fitting 42 during use of the tamponade balloon catheter assembly 2, the hub lumen 40 may also provide an opening for receiving the inflation port or side arm 20 extending from the proximal end 13 of the catheter 8. The side arm 20 can be removably secured within the hub lumen 40 of the introducer device 12 as shown in FIG. 8 and FIG. 11, such as by friction fit or interference fit, during insertion of the tamponade balloon catheter assembly 2 into the uterus 4 via the transabdominal approach. The hub 22 may include other openings or apertures in addition to lumen 40 to allow for additional points of drainage or inflation and/or to allow additional tubes or catheters to be removably attached to the hub 22 and placed into fluid communication with the catheter 8 when the introducer device 12 is coupled to the tamponade balloon catheter assembly 2 as shown in FIG. 6.

When the balloon 6 is deployed within the uterine cavity, the outward force of the balloon 6 against the uterine wall helps to resist dislodgement of the balloon 6 from the uterus 4. However, the rigidity provided to the catheter 8 of the tamponade balloon catheter assembly 2 by the internal stylet 10 reduces and/or mitigates longitudinal collapse of the catheter 8, such that at least the portion of the catheter 8 located between the balloon 6 and the hub 22 of the introducer device 12 will maintain structural integrity and longitudinal length. This reduces and/or mitigates longitudinal shrinkage or collapse of the longitudinal catheter body 9 when force is exerted on it in either a proximal and/or distal direction, such as in the event that the uterus 4 attempts to "deliver" the balloon 6 through an insufficient cervix (thus exerting pressure on the catheter body 9 in a proximal direction) and/or when a physician pushes the catheter 8 into the uterus 4 during insertion (thus exerting pressure on the catheter body 9 in a distal direction). In essence, the stylet 10 provides a scaffold to bolster the catheter 8 during introduction, positioning and use of the tamponade balloon catheter assembly 2.

Turning now to FIGS. 1 and 8, introduction of a tamponade balloon catheter assembly 2 such as the Bakri balloon catheter, with an introducer device 12, may be as described below. Before the uterine tamponade balloon catheter assembly 2 is inserted into a patient, the introducer device 12 may be inserted into the proximal end 13 of the tamponade balloon catheter assembly 2 and the hub 22 coupled to the proximal end 13 of the tamponade balloon catheter assembly 2. Alternatively, the introducer device 12 may be pre-loaded into the tamponade balloon catheter assembly 2 so that the tamponade balloon catheter assembly 2 coupled to the introducer device 12 is ready to use as a unit right out of the package. As shown in FIGS. 8 and 11, the inflation port or side arm 20 at the proximal end 13 of the tamponade balloon catheter assembly 2 can be inserted into the proximal end 30 of the hub 22 and removably secured within the hub lumen 40 of the introducer device 12 during insertion of the tamponade balloon catheter assembly 2 into the uterus 4, such as by friction fit or interference fit. In other words, with the hub 22 of the introducer device 12 located just proximal to the proximal end 13 of the tamponade balloon catheter assembly 2, the side arm 20 of the tamponade balloon catheter assembly 2 that provides a port for inflation of the balloon 6 during use can be tucked into the hub lumen 40 to maintain the tamponade balloon catheter assembly 2 in a low profile and compact delivery configuration to prevent the side arm 20 from interfering with the introduction of the tamponade balloon catheter assembly 2 or from snagging on tissue, especially during a "hub-first" trans-abdominal insertion into the uterus as shown in FIG. 8.

Following a vaginal birth, the tamponade balloon catheter assembly 2, with the introducer device 12 in place within a lumen of the tamponade balloon catheter assembly 2, may be inserted "balloon first" through the vagina 5 and into the uterus 4 as shown in FIG. 1. Alternatively, following a cesarean birth, the tamponade balloon catheter assembly 2, coupled to an introducer device 12 in place within a lumen of the tamponade balloon catheter assembly 2, may be inserted "hub first" through the abdominal incision as shown in FIG. 8. The hub 22 and the proximal end 13 of the tamponade balloon catheter assembly 2 can be pulled through the vaginal canal until the base of the balloon 6 contacts the internal cervical ostium.

With the balloon 6 in its desired position in the uterus 4, the side arm 20 can be removed from its position where it has been tucked and held within the hub lumen 40. The balloon 6 may then be inflated or otherwise expanded with a physiologically suitable fluid through the inflation lumen 14 of catheter 8. The shape of the fully expanded balloon 6 will generally conform to the shape of the interior of the uterus 4, and preferably the lower uterine segment, thus exerting a compressive force against the uterine walls. In one example, the balloon 6 may be quickly and carefully inflated with 200 to 500 milliliters of saline. The balloon 6 may be partially or fully deflated to allow repositioning, if necessary. Packing may also be added to the vagina 5, or traction may be applied to the shaft of the catheter 8 to increase effectiveness of the tamponade balloon catheter assembly 2.

The introducer device 12 may remain in place within the drainage lumen 16 of the tamponade balloon catheter assembly 2 during use, if desired. Blood or other fluids draining in a proximal direction through the catheter 8 from the uterus 4 may flow through the lumen 40 formed in the hub 22 and exit the proximal end 30 of the hub 22 through hub lumen 40. As shown in FIGS. 1 and 6, a drainage tube 44 is removably attached to the hub lumen 40 by a drainage adapter fitting 42 that has been inserted into the hub lumen 40 and is snugly and securely held in place in the hub lumen 40 such as by friction fit, interference fit or other suitable attachment means or mechanisms. The hub 22 is sufficiently pliable and flexible to allow the user to squeeze or otherwise manipulate at least the proximal end 30 to open or widen the hub lumen 40 to allow for the ease of insertion and removal of a drainage adaptor fitting 42 (as well as insertion and removal of the side arm 20 as described above) and any other tubes, adaptors, fittings or accessory devices that the user may wish to place into fluid communication with the hub lumen 40. However, other suitable mechanisms for securing the drainage adaptor fitting 42 in place may be used. Blood and other fluids draining proximally through the hub 22 can continue flowing through the drainage adaptor fitting 42 and into the drainage tube 44 for collection in waste collection bag 11. The volume and flow of fluid into the waste collection bag 11 can be monitored to determine when hemorrhage is reduced or has ceased. Upon adequate cessation of hemorrhage as determined by the physician, the balloon 6 may be quickly drained through the drainage lumen 16 to deflate the balloon. The tamponade balloon catheter assembly 2 can then be removed from the patient trans-vaginally.

Throughout this specification, unless the context requires otherwise, the words "comprise" and "include" and variations such as "comprising" and "including" will be understood to imply the inclusion of an item or group of items, but not the exclusion of any other item or group items.

While various embodiments of the invention have been described, it will be apparent to those of ordinary skill in the art that many more embodiments and implementations are possible within the scope of the invention. Furthermore, although various indications have been given as to the scope of this invention, the invention is not limited to any one of these but may reside in two or more of these combined together. Accordingly, the invention is not to be restricted except in light of the attached claims and their equivalents.

We claim:

1. A catheter assembly comprising:
a positioning device comprising:
a stylet having a proximal end and a distal end; and
a hub at the proximal end of the stylet, wherein the hub comprises an open proximal end, an open distal end, and a hub lumen extending the entire distance between the open proximal and open distal ends, wherein the open proximal end is configured to receive fluid flow from the hub lumen, through the open proximal end, and out of the open proximal end, and
a tamponade balloon catheter comprising:
a catheter comprising a proximal end and a distal end and at least one lumen extending there between, wherein the catheter comprises at least one echogenic element disposed thereon; and
an expandable tamponade device disposed about at least a portion of the catheter;
wherein the stylet is configured to extend longitudinally within at least a portion of the at least one catheter lumen; and
wherein, when the stylet is disposed within at least the portion of the at least one catheter lumen, the open proximal end remains open and the open distal end of the hub is configured to receive fluid flow from the at least one catheter lumen.

2. The assembly of claim 1 wherein the at least one echogenic element is positioned at the distal end of the catheter.

3. The assembly of claim 1 wherein the at least one echogenic element comprises a plurality of echogenic beads.

4. The assembly of claim 3 wherein the plurality of echogenic beads are embedded in a polymeric material.

5. The assembly of claim 4 wherein the polymeric material is over-molded on to the distal end of the catheter.

6. The assembly of claim 3 wherein the plurality of echogenic beads are formed from at least one of glass, polymeric material, metals and combinations thereof.

7. The assembly of claim 1 wherein the at least one echogenic element comprises a polymeric coating.

8. The assembly of claim 1 wherein the at least one echogenic element is coupled to the catheter by at least one of bonding, RF welding, adhesives, over-molding and mechanical attachment mechanisms.

9. The assembly of claim 1 wherein the hub further comprises a sidewall extending between the open proximal end and the open distal end defining a hub lumen, wherein the sidewall comprises a first portion having a first thickness and a second portion comprising a second thickness, wherein the second thickness is greater than the first thickness, and wherein the stylet is coupled to the second portion.

10. The assembly of claim 1 wherein the hub further comprises a sidewall extending between the open proximal end and the open distal end defining a hub lumen, wherein the sidewall of the hub comprises an outer surface, and wherein at least a portion of the outer surface comprises at least one of threads, ribs, coupling mechanisms, barbs, flanges, channels and projections.

11. The assembly of claim 1 wherein the proximal end of the catheter further comprises an inflation port and wherein a proximal end of the inflation port is configured to be removably received within the hub lumen.

* * * * *